(12) United States Patent
Kim et al.

(10) Patent No.: US 9,078,590 B2
(45) Date of Patent: Jul. 14, 2015

(54) PROVIDING ADDITIONAL INFORMATION CORRESPONDING TO CHANGE OF BLOOD FLOW WITH A TIME IN ULTRASOUND SYSTEM

(75) Inventors: Sung Hee Kim, Seoul (KR); Suk Jin Lee, Seoul (KR)

(73) Assignee: SAMSUNG MEDISON CO., LTD., Hongchun-Gun, Kangwon-Do (KR)

( * ) Notice: Subject to any disclaimer, the term of this patent is extended or adjusted under 35 U.S.C. 154(b) by 63 days.

(21) Appl. No.: 13/311,274

(22) Filed: Dec. 5, 2011

(65) Prior Publication Data

US 2012/0078108 A1   Mar. 29, 2012

(30) Foreign Application Priority Data

Dec. 7, 2010   (KR) .................... 10-2010-0123899

(51) Int. Cl.
*A61B 8/08*   (2006.01)
*A61B 8/06*   (2006.01)
*A61B 8/13*   (2006.01)
*A61B 8/00*   (2006.01)

(52) U.S. Cl.
CPC ... *A61B 8/06* (2013.01); *A61B 8/08* (2013.01); *A61B 8/13* (2013.01); *A61B 8/469* (2013.01); *A61B 8/488* (2013.01); *A61B 8/5238* (2013.01); *A61B 8/0891* (2013.01)

(58) Field of Classification Search
CPC ... G01S 7/52071; G01S 15/8988; A61B 8/06; A61B 8/13; A61B 8/463; A61B 8/488; G01F 1/663

USPC .......... 600/437, 440, 443, 447, 454; 348/169, 348/699; 382/107, 207, 236; 128/916
See application file for complete search history.

(56) References Cited

U.S. PATENT DOCUMENTS 5,243,987 A *   9/1993   Shiba ........................... 600/463
5,709,211 A     1/1998   Machida
(Continued)

FOREIGN PATENT DOCUMENTS

EP     1 977 694 A1    10/2008
JP     2006-520619      9/2006
(Continued)

OTHER PUBLICATIONS

European Search Report issued in European Patent Application No. 11191707.6 dated Mar. 20, 2012.
(Continued)

*Primary Examiner* — Elmer Chao
(74) *Attorney, Agent, or Firm* — McDermott Will & Emery LLP

(57) ABSTRACT

There are provided embodiments for providing additional information. In one embodiment, an ultrasound system comprises: an ultrasound data acquisition unit configured to acquire first ultrasound data and second ultrasound data corresponding to a living body; and a processing unit configured to form a brightness mode image based on the first ultrasound data, set at least one sample volume on the brightness mode image, and form blood flow information corresponding to blood flow in the living body based on the second ultrasound data corresponding to the at least one sample volume, the processing unit being further configured to form additional information corresponding to a change of the blood flow with a time based on the blood flow information.

6 Claims, 5 Drawing Sheets

(56) References Cited

U.S. PATENT DOCUMENTS

| | | | |
|---|---|---|---|
| 6,077,226 A | 6/2000 | Washburn et al. | |
| 6,177,923 B1* | 1/2001 | Arenson et al. | 345/589 |
| 7,621,872 B2* | 11/2009 | Hyun | 600/443 |
| 2003/0013963 A1* | 1/2003 | Bjaerum et al. | 600/443 |
| 2006/0241458 A1 | 10/2006 | Hayashi et al. | |
| 2008/0091107 A1 | 4/2008 | Kim | |
| 2008/0249411 A1 | 10/2008 | Kye et al. | |
| 2009/0062653 A1* | 3/2009 | Hyun | 600/454 |

FOREIGN PATENT DOCUMENTS

| | | |
|---|---|---|
| JP | 2007-514477 A | 6/2007 |
| JP | 2008-100061 | 5/2008 |
| KR | 10-2008-0090888 A | 10/2008 |
| WO | WO 2004/072676 | 8/2004 |
| WO | WO-2005/054898 A1 | 6/2005 |

OTHER PUBLICATIONS

Korean Office Action issued in Korean Application No. 10-2010-0123899 dated Apr. 29, 2013.

Korean Office Action, w/ English translation thereof, issued in Korean Patent Application No. KR 10-2010-0123899 dated Nov. 28, 2013.

* cited by examiner

PROVIDING ADDITIONAL INFORMATION CORRESPONDING TO CHANGE OF BLOOD FLOW WITH A TIME IN ULTRASOUND SYSTEM

CROSS-REFERENCE TO RELATED APPLICATION

The present application claims priority from Korean Patent Application No. 10-2010-0123899 filed on Dec. 7, 2010, the entire subject matter of which is incorporated herein by reference.

TECHNICAL FIELD

The present disclosure generally relates to ultrasound systems, and more particularly to providing additional information corresponding to a change of blood flow with a time in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of a target object (e.g., human organs).

The ultrasound system may provide ultrasound images of various modes including a brightness mode (B mode) image representing reflection coefficients of the ultrasound signals reflected from a target object of a living body with a 2D (two-dimensional) image, a Doppler mode (D mode) image representing speed of a moving target object with spectral Doppler by using a Doppler effect, a color Doppler mode (C mode) image representing speed of a moving target object with colors by using the Doppler effect, and an elastic mode (E mode) image representing mechanical characteristics of tissues object before and after applying a pressure thereto. Particularly, the ultrasound system may transmit and receive ultrasound signals to and from the living body to thereby form Doppler signals corresponding to a sample volume, which is set on a B mode image. The ultrasound system may further form the D mode image (i.e., Doppler spectrum image) that represents the speed of the moving target object such as blood flow, heart, etc. with Doppler spectrums based on the Doppler signals.

The ultrasound system may provide the Doppler spectrum image only based on the blood flow information. Thus, it is required to provide additional information corresponding to a change of the blood flow with a time to enhance the convenience of a user.

SUMMARY

There are provided embodiments for providing additional information corresponding to a change of blood flow with a time in an ultrasound system.

In one embodiment, by way of non-limiting example, an ultrasound system comprises: an ultrasound data acquisition unit configured to acquire first ultrasound data and second ultrasound data corresponding to a living body; and a processing unit configured to form a brightness mode image based on the first ultrasound data, set at least one sample volume on the brightness mode image, and form blood flow information corresponding to blood flow in the living body based on the second ultrasound data corresponding to the at least one sample volume, the processing unit being further configured to form additional information corresponding to a change of the blood flow with a time based on the blood flow information.

In another embodiment, there is provided a method of providing additional information, comprising: a) acquiring first ultrasound data corresponding to a living body; b) forming a brightness mode image based on the first ultrasound data; c) setting at least one sample volume on the brightness mode image; d) acquiring second ultrasound data corresponding to the at least one sample volume; e) forming blood flow information corresponding to blood flow in the living body based on the second ultrasound data corresponding to the at least one sample volume; and f) forming additional information corresponding to a change of the blood flow with a time based on the blood flow information.

This summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
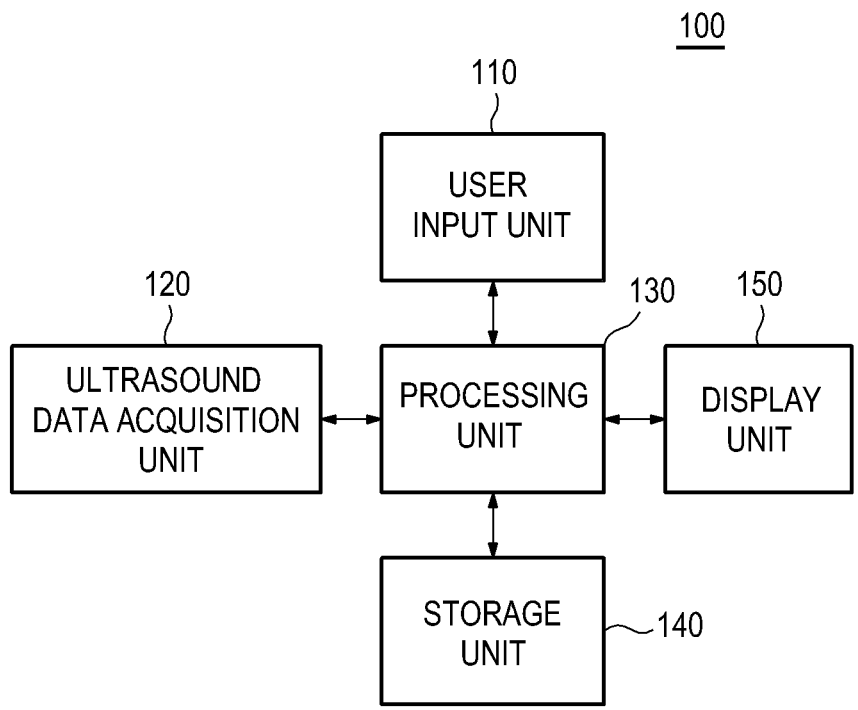
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110.

Figure 2:
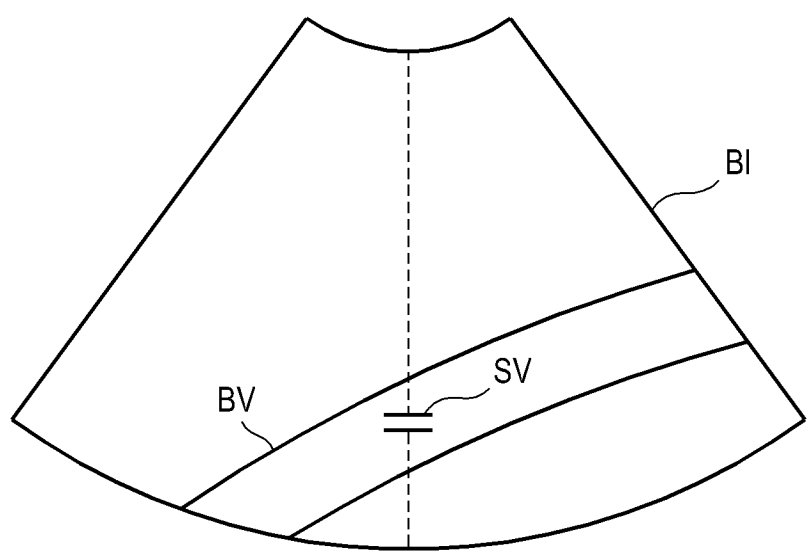
FIG. 2 is a schematic diagram showing an example of a brightness mode image and a sample volume.

The user input unit 110 may be configured to receive input information. In the embodiment, the input information may include sample volume setting information for setting a sample volume SV on a brightness mode image BI, as shown in FIG. 2. However, it should be noted herein that the input information may not be limited thereto. In FIG. 2, reference numeral BV represents a blood vessel. The user input unit 110 may include a control panel, a trackball, a mouse, a keyboard and the like.

The ultrasound system 100 may further include an ultrasound data acquisition unit 120. The ultrasound acquisition unit 120 may be configured to transmit ultrasound signals to a living body. The living body may include target objects (e.g., blood flow, a heart, etc.). The ultrasound acquisition unit 120 may be further configured to receive ultrasound signals (i.e., ultrasound echo signals) from the living body to acquire ultrasound data.

Figure 3:
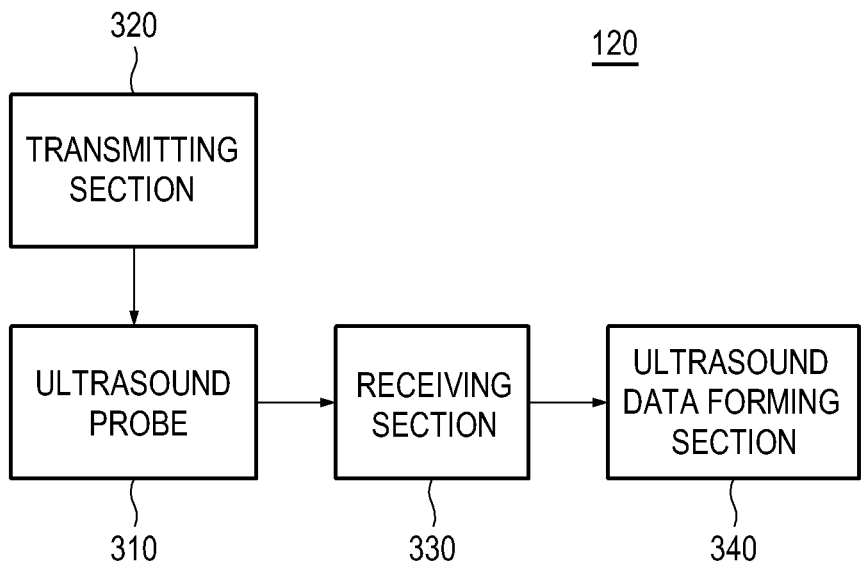
FIG. 3 is a block diagram showing an illustrative embodiment of an ultrasound data acquisition unit.

FIG. 3 is a block diagram showing an illustrative embodiment of the ultrasound data acquisition unit. Referring to FIG. 3, the ultrasound data acquisition unit 120 may include an ultrasound probe 310.

The ultrasound probe 310 may include a plurality of transducer elements (not shown) for reciprocally converting between ultrasound signals and electrical signals. The ultrasound probe 310 may be configured to transmit the ultrasound signals to the living body. The ultrasound probe 310 may be further configured to receive the ultrasound echo signals from the living body to output received signals. The received signals may be analog signals. The ultrasound probe 310 may include a convex probe, a linear probe and the like.

The ultrasound data acquisition unit 120 may further include a transmitting section 320. The transmitting section 320 may be configured to control the transmission of the ultrasound signals. The transmitting section 320 may be further configured to generate electrical signals ("transmitting signals") for obtaining an ultrasound image in consideration of the elements and focusing points. The transmitting section 320 may include a transmitting signal generating section (not shown), a transmitting delay information memory (not shown), a transmitting beam former (not shown) and the like.

In the embodiment, the transmitting section 320 may generate first transmitting signals for obtaining the brightness mode image BI. Thus, the ultrasound probe 310 may convert the first transmitting signals into the ultrasound signals, transmit the ultrasound signals to the living body and receive the ultrasound echo signals from the living body to thereby output first received signals. The transmitting section 320 may further generate second transmitting signals for obtaining a Doppler spectrum image corresponding to the sample volume SV. Thus, the ultrasound probe 310 may convert the second transmitting signals into the ultrasound signals, transmit the ultrasound signals to the living body and receive the ultrasound echo signals from the living body to thereby output second received signals.

The ultrasound data acquisition unit 120 may further include a receiving section 330. The receiving section 330 may be configured to convert the received signals into digital signals. The receiving section 330 may be further configured to apply delays to the digital signals in consideration of the elements and the focusing points to thereby output digital receive-focused signals. The receiving section 330 may include an analog-to-digital converter (not shown), a receiving delay time information memory (not shown), a receiving beam former (not shown) and the like.

In the embodiment, the receiving section 330 may convert the first received signals provided from the ultrasound probe 310 into first digital signals. The receiving section 330 may further apply delays to the first digital signals in consideration of the elements and the focusing points to thereby output first digital receive-focused signals. The receiving section 330 may further convert the second received signals provided from the ultrasound probe 310 into second digital signals. The receiving section 330 may further apply delays to the second digital signals in consideration of the elements and the focusing points to thereby output second digital receive-focused signals.

The ultrasound data acquisition unit 120 may further include an ultrasound data forming section 340. The ultrasound data forming section 340 may be configured to form ultrasound data corresponding to the ultrasound image based on the digital receive-focused signals provided from the receiving section 330. The ultrasound data forming section 340 may be further configured to perform a signal process (e.g., gain control, etc) upon the digital receive-focused signals.

In the embodiment, the ultrasound data forming section 340 may form first ultrasound data corresponding to the brightness mode image BI based on the first digital receive-focused signals provided from the receiving section 330. The first ultrasound data may include radio frequency data. However, it should be noted herein that the first ultrasound data may not be limited thereto. The ultrasound data forming section 340 may further form second ultrasound data corresponding to the sample volume SV (i.e., Doppler spectrum image) based on the second digital receive-focused signals provided from the receiving section 330. The second ultrasound data may include the radio frequency data or in-phase/quadrature data. However, it should be noted herein that the second ultrasound data may not be limited thereto.

Referring back to FIG. 1, the ultrasound system 100 may further include a processing unit 130 in communication with the user input unit 110 and the ultrasound data acquisition unit 120. The processing unit 130 may include a central processing unit, a microprocessor, a graphic processing unit and the like.

Figure 4:
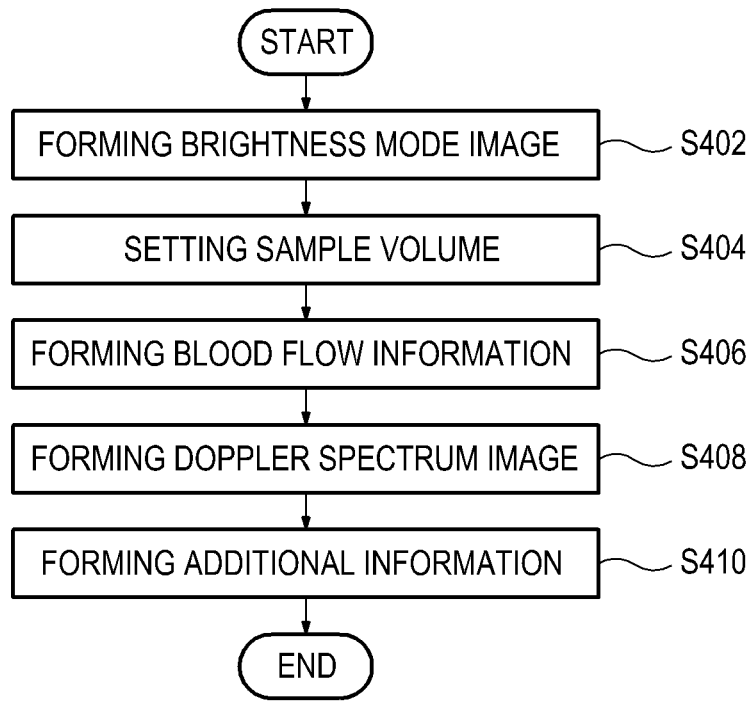
FIG. 4 is a flow chart showing a process of forming a Doppler spectrum image and additional information.

FIG. 4 is a flow chart showing a process of forming additional information. The processing unit 130 may be configure to form the brightness mode image BI based on the first ultrasound data provided from the ultrasound data acquisition unit 120, at step S402 in FIG. 4. The brightness mode image BI may be displayed on a display unit 150. Thus, the user may set the sample volume SV on the brightness mode image BI by using the user input unit 110.

The processing unit 130 may be configured to set the sample volume SV on the brightness mode image BI as shown in FIG. 2, based on the input information provided from the user input unit 110, at step S404 in FIG. 4. Thus, the ultrasound data acquisition unit 120 may acquire the second ultrasound data corresponding to the sample volume SV.

The processing unit 130 may be configured to form information (hereinafter, "blood flow information") corresponding to a moving target object (i.e., blood flow) in the living body based on the second ultrasound data provided from the ultrasound data acquisition unit 120, at step S406 in FIG. 4. In the embodiment, the blood flow information may include blood flow velocity information, blood flow rate information, blood flow velocity distribution information and the like. The methods of forming the blood flow information are well known in the art. Thus, they have not been described in detail so as not to unnecessarily obscure the present invention.

The processing unit 130 may be configured to form the Doppler spectrum image based on the blood flow information, at step S408 in FIG. 4. The methods of forming the Doppler spectrum image are well known in the art. Thus, they have not been described in detail so as not to unnecessarily obscure the present invention.

The processing unit 130 may be configured to form additional information based on the blood flow information, at step S410 in FIG. 4. The additional information may be information for representing a change of the blood flow with a time.

Figure 5:
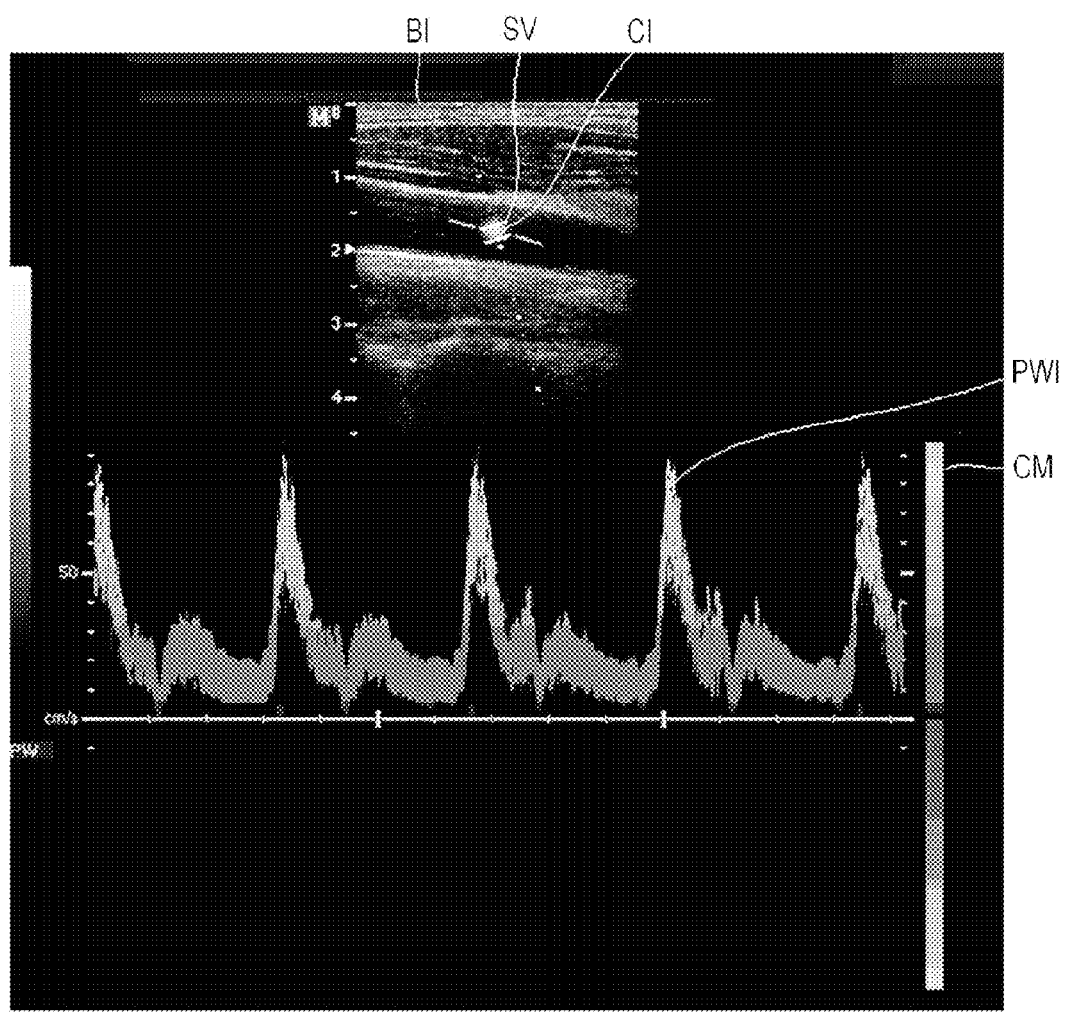
FIG. 5 is a schematic diagram showing an example of the additional information.

As one example, the processing unit 130 may form a color map CM as the additional information based on the blood flow information, as shown in FIG. 5. The color map CM may be formed by mapping a plurality of blood flow velocities (i.e., height of Doppler spectrum) to colors.

As another example, the processing unit 130 may form a color Doppler spectrum image PWI as the additional information based on the blood flow information, as shown in FIG. 5. The color Doppler spectrum image PWI may be formed by mapping the colors corresponding to the color map CM to the Doppler spectrum image. That is, the color Doppler spectrum image PWI may be formed by applying the colors corresponding to the blood flow velocities to pixels of the Doppler spectrum image.

As yet another example, the processing unit 130 may form a color blood flow velocity image CI as the additional information based on the blood flow information, as shown in FIG. 5. The color blood flow velocity image CI may be formed by mapping the blood flow velocity to the color. That is, the color blood flow velocity image CI may be formed by mapping the blood flow velocity corresponding to current blood flow information to the color.

Although it is described that the processing unit 130 forms the color map, the color Doppler spectrum image or the color blood flow velocity image, the processing unit 130 may form at least one of the color map, the color Doppler spectrum image and the color blood flow velocity image.

As yet another example, the processing unit 130 may apply transparency corresponding to the blood flow rate to at least one of the color map, the color Doppler spectrum image and the color blood flow velocity image as the additional information, based on the blood flow information. That is, the processing unit 130 may apply the transparency to the colors corresponding to the blood flow velocities based on the blood flow rate.

Figure 6:
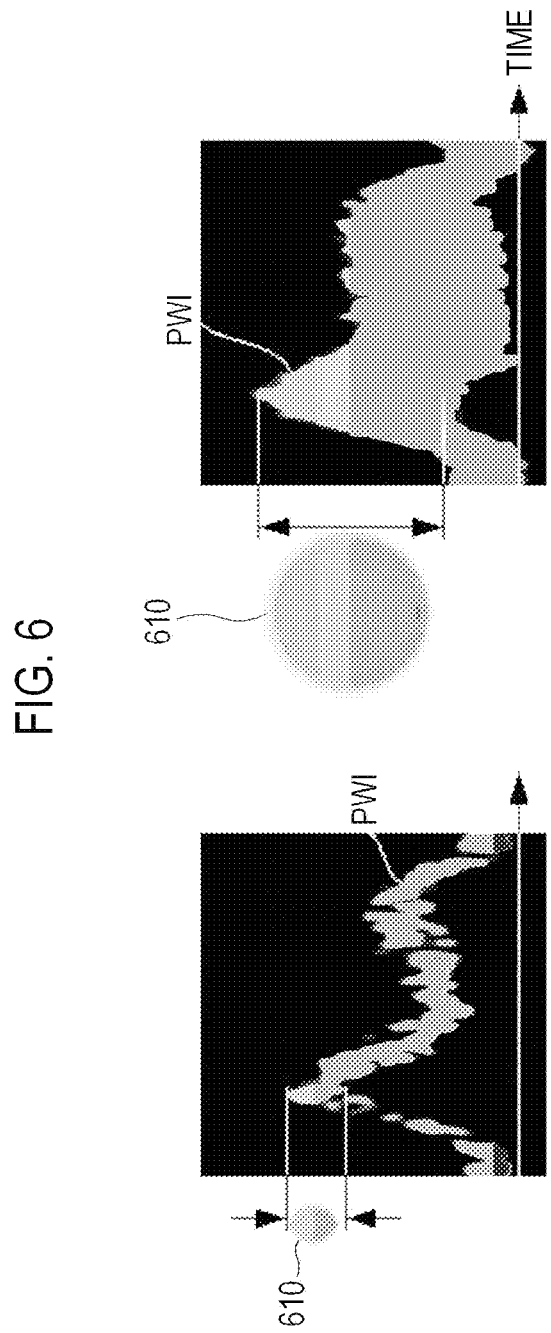
FIG. 6 is a schematic diagram showing another example of the additional information.

As yet another example, the processing unit 130 may form a blood flow velocity distribution image 610 as the additional information based on the blood flow information, as shown in FIG. 6. The blood flow velocity distribution image 610 may be an image for representing blood flow velocity distribution based on distribution of spots (i.e., width of Doppler spectrum).

As yet another example, the processing unit 130 may form numeric information corresponding to the blood flow velocity and variance as the additional information based on the blood flow information.

Although it is described that the processing unit 130 forms the Doppler spectrum image with the additional information based on the blood flow information, the processing unit 130 may form the additional information based on the blood flow information.

Figure 7:
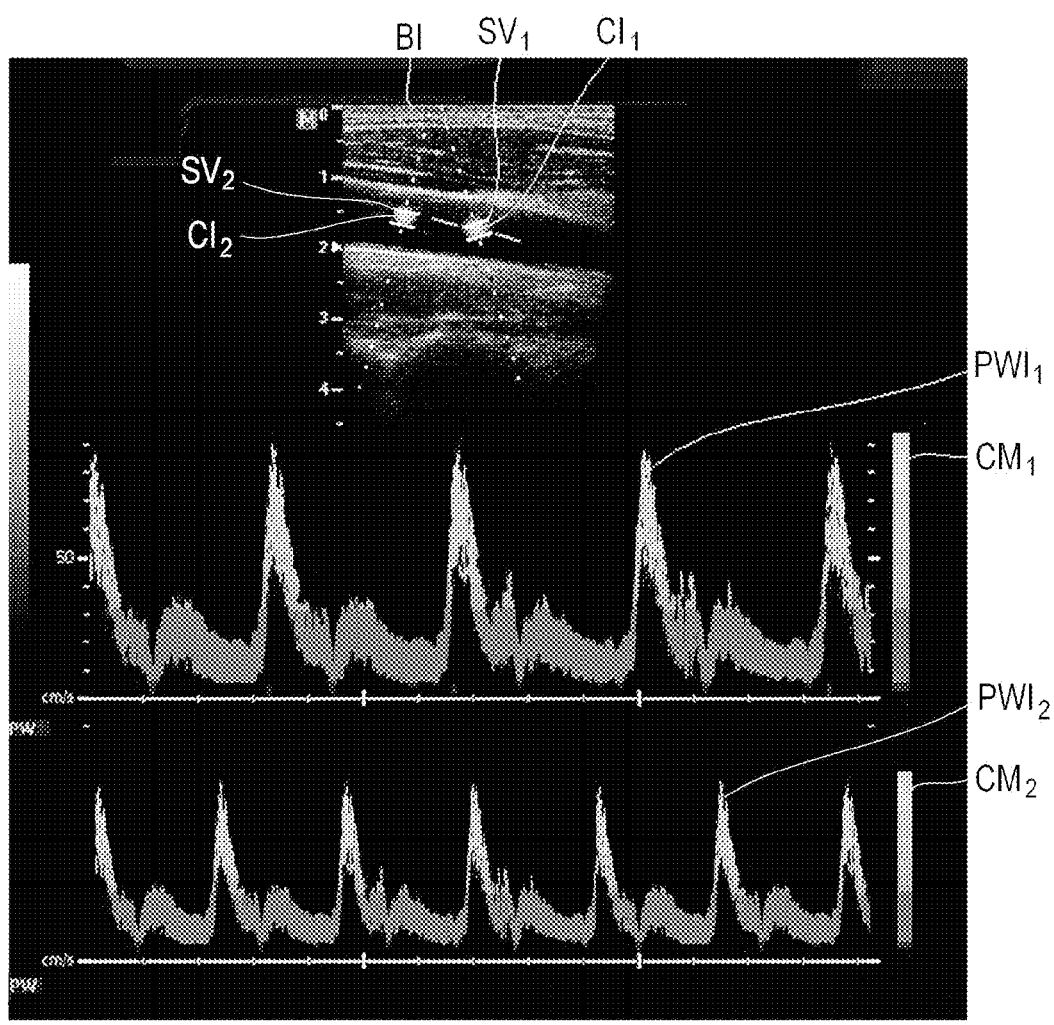
FIG. 7 is a schematic diagram showing yet another example of the additional information.

Also, although it is described that the sample volume SV is set on the brightness mode image BI and the additional information corresponding to the sample volume is provided, at least one sample volume (e.g., two sample volumes $SV_1$, $SV_2$ as shown in FIG. 7) is set on the brightness mode image BI and the additional information (e.g., color Doppler spectrum images $PWI_1$, $PWI_2$, color blood flow images $CI_1$, $CI_2$ and the like) corresponding to each of the sample volumes $SV_1$, $SV_2$.

Referring back to FIG. 1, the ultrasound system 100 may further include a storage unit 140. The storage unit 140 may store the ultrasound data (i.e., first ultrasound data and second ultrasound data) acquired by the ultrasound data acquisition unit 120. The storage unit 140 may further store the input information received by the user input unit 110.

The ultrasound system 100 may further include the display unit 150. The display unit 150 may be configured to display the brightness mode image BI formed by the processing unit 130. The display unit 150 may be further configured to display the Doppler spectrum image formed by the processing unit 130. The display unit 150 may be further configured to display the additional information formed by the processing unit 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising;
   an ultrasound data acquisition unit configured to acquire first ultrasound data and second ultrasound data corresponding to a living body; and
   a processor configured to form a brightness mode image based on the first ultrasound data, set at least two sample volumes on the brightness mode image, control the ultrasound data acquisition unit to acquire the second ultrasound data in the at least two sample volumes in response to the at least two sample volumes being set on the brightness mode image, and form blood flow information corresponding to blood flow in the living body based on the second ultrasound data corresponding to the at least two sample volumes, wherein the blood flow information includes blood flow velocity information, blood flow rate information, and blood flow velocity distribution information,
   the processor being further configured to form and display additional information based on the blood flow information, wherein the additional information comprises additional information corresponding to a first sample volume included in the at least two sample volumes and additional information corresponding to a second sample volume included in the at least two sample volumes and the additional information corresponding to the first sample volume and the additional information corresponding to the second sample volume are displayed separately,
   wherein the additional information formed by the processor comprises color maps corresponding to each of the first sample volume and the second sample volume, the color maps are formed by mapping blood flow velocities to colors based on the blood flow information, wherein the color maps assign a different color to each different velocity value;
   wherein the additional information formed by the processor further comprises color plots of the Doppler spectrums corresponding to each of the first sample volume and the second sample volume, in which a plurality of colors corresponding to heights of the Doppler spectrums are applied to pixels of Doppler spectrum images according to the different colors assigned by the color maps, and the Doppler spectrum images comprise the color plots of the Doppler spectrums representing blood flow velocities against time based on the blood flow velocity information, wherein the Doppler spectrums are plotted on a vertical axis and time is plotted on a horizontal axis,
   the additional information further comprises Ran color blood flow velocity images corresponding to each of the first sample volume and the second sample volume, which are displayed on the first sample volume and the second sample volume simultaneously with display of the color plots of the Doppler spectrums, and are formed by applying colors corresponding to blood flow velocities to the first sample volume and the second sample volume according to the different colors assigned by the color maps and based on the blood flow velocity information, and the processor is further configured to apply transparency to at least one of the color maps, the color plots of the Doppler spectrums, and the color blood flow velocity images as the additional information based on the blood flow rate information, to term t blood flow velocity distribution image for representing blood flow velocity distribution corresponding to distribution of spots as the additional information based on the blood flow velocity distribution information, and to form numeric information corresponding to blood flow velocity and variance as the additional information based on the blood flow velocity information.

2. The ultrasound system of claim 1, wherein the color blood flow velocity images are displayed on the first sample volume and the second sample volume on the brightness mode image.

3. A method of providing additional information in an ultrasound system, the method comprising:

a) acquiring, by an ultrasound data acquisition unit of the ultrasound system, first ultrasound data corresponding to a living body;

b) forming a brightness mode image based on the first ultrasound data;

c) setting at least two sample volumes on the brightness mode image;

d) in response to the setting of the at least two sample volumes on the brightness mode image, acquiring, by the ultrasound data acquisition unit of the ultrasound system, second ultrasound data corresponding to the at least two sample volumes;

e) forming blood flow information corresponding to blood flow in the living body based on the second ultrasound data corresponding to the at least two sample volumes, wherein the blood flow information includes blood flow velocity information, blood flow rate information, and blood flow velocity distribution information; and f) forming additional information based on the blood flow information, wherein the additional information comprises, additional information corresponding to a first sample volume included in the at least two sample volumes and additional information corresponding to a second sample volume included in the at least two sample volumes, and the additional information corresponding to the first sample volume and the additional information corresponding to the second sample volume are displayed separately, wherein the additional information comprises color maps corresponding to each of the first sample volume and the second sample volume, the color mans are formed by mapping blood flow velocities to colors based on the blood flow information, wherein the color maps assign a different color to each different velocity, wherein the additional information further comprises plots of the Doppler spectrums corresponding to each of the first sample volume and the second sample volume, in which a plurality of colors corresponding to heights of the Doppler spectrums are applied to pixels of Doppler spectrum images according to the different colors assigned by the color maps, and the Doppler spectrum images comprise the color plots of the Doppler spectrums representing blood flow velocities against time based on the blood flow velocity information, wherein the Doppler spectrums are plotted on a vertical axis and time is plotted on a horizontal axis, wherein the additional information further comprises color blood flow velocity images, corresponding to each of the first sample volume and the second sample volume, which are displayed on the first sample volume and the second sample volume simultaneously with display of the color plots of the Doppler spectrums, and are formed by applying colors corresponding to the blood flow velocities to the first sample volume and the second sample volume according to the different colors assigned by the color maps and based on the blood flow velocity information, and wherein the step f) further comprises applying transparency to at least one of the color maps, the color plots of the Doppler spectrums, and the color blood flow velocity images as the additional information based on the blood flow rate information, forming a blood flow velocity distribution image for representing, blood flow velocity distribution corresponding to distribution of spots as the additional information based on the blood flow velocity distribution information, and forming numeric information corresponding to blood flow velocity and variance as the additional information based on the blood flow velocity information.

4. The method of claim 3, wherein the color blood flow velocity images are displayed on the first sample volume and the second sample volume cm the brightness mode image.

5. The ultrasound system of claim 1, wherein the color plot of the Doppler spectrums are plots having the Doppler spectrums plotted along, a y-axis and time plotted along an x-axis.

6. The method of claim 3, wherein the color plot of the Doppler spectrums are plots having the Doppler spectrums plotted along a y-axis and time plotted along an x-axis.

* * * * *